United States Patent [19]

Pollak et al.

[11] Patent Number: 5,159,410
[45] Date of Patent: Oct. 27, 1992

[54] METHOD FOR IN-SITU DETERMINATION OF THE FERMI LEVEL IN GAAS AND SIMILAR MATERIALS BY PHOTOREFLECTANCE

[76] Inventors: Fred H. Pollak, 531 Main St., New York, N.Y. 10044; J. M. Woodall, 10 Upland Rd. North, Bedford, N.Y. 10506; P. A. Montano, 1 Tiffany Pl., Brooklyn, N.Y. 11201

[21] Appl. No.: 563,094

[22] Filed: Aug. 3, 1990

Related U.S. Application Data

[63] Continuation-in-part of Ser. No. 408,903, Sep. 13, 1989, which is a continuation-in-part of Ser. No. 382,191, Jul. 20, 1989.

[51] Int. Cl.$^5$ .......................................... G01N 21/25
[52] U.S. Cl. .................................... 356/417; 356/432
[58] Field of Search .................. 356/417, 432, 432 T, 356/445

[56] References Cited

U.S. PATENT DOCUMENTS 4,953,983  9/1990  Bottka et al. .................... 356/432 T Primary Examiner—Richard A. Rosenberger
Assistant Examiner—K. P. Hantis
Attorney, Agent, or Firm—Paul M. Craig, Jr.

[57] ABSTRACT

A method for in-situ determination by photoreflectance of the Fermi level ($V_F$) at the surfaces or interfaces of GaAs and related materials, in which a probe beam of monochromatic light and a modulated pump beam from a pump source are directed onto a sample, and the measured barrier height $V_m = V_F - V_S$ is obtained from the information in the reflected light, where $V_S$ represents the surface voltage effects on the sample by the photoreflectance, whereby $V_m$ approaches $V_F$ as $V_S$ approaches zero during repeated tests in which a parameter such as temperature affecting the numerical value of $V_S$ is changed until there is flattening of the curve illlustrating $V_m$ as a function of the parameter.

10 Claims, 4 Drawing Sheets

METHOD FOR IN-SITU DETERMINATION OF THE FERMI LEVEL IN GAAS AND SIMILAR MATERIALS BY PHOTOREFLECTANCE

This application is a continuation-in-part application of the copending application Ser. No. 07/408,903, filed Sep. 13, 1989 and entitled "Method and Apparatus for Determining a Material's Characteristics by Photoreflectance Using Improved Computer Control," which is a continuation-in-part application of the copending application Ser. No. 07/382,191, filed Jul. 20, 1989 and entitled "Method and Apparatus for Determining a Material's Characteristics by Photoreflectance."

FIELD OF INVENTION

The present invention relates to a method for determining in-situ the Fermi level in GaAs and similar materials by the use of photoreflectance.

BACKGROUND OF THE INVENTION

The importance to study and characterize semiconductors (bulk or thin film), semiconductor heterostructures (superlattices, quantum wells, heterojunctions) and semiconductor interfaces (Schottky barriers, metal-insulator-semiconductors, semiconductor-electrolyte, semiconductor-vacuum, etc.) assumes ever-greater significance, particularly as many of these semiconductors and semiconductor microstructures are fabricated by modern thin-film techniques such as molecular beam epitaxy (MBE), metal-organic chemical vapor deposition (MOCVD), etc.

The materials and interfaces grown by MBE and MOCVD as well as other methods can be characterized by a variety of optical, electronic and structural methods including photoluminescence, photoluminescence excitation spectroscopy, absorption spectroscopy, modulation spectroscopy, Raman and resonant Raman scattering, cyclotron resonance, Hall effect, transmission electron microscopy, etc. Each of these tools provides specific information about the material of interest. For characterization purposes the experimental tools should be as simple and informative as possible. Many of the methods mentioned above are specialized and sometimes difficult to employ. For example, a number thereof, such as photoluminescence, photoluminescence excitation spectroscopy, absorption, cyclotron resonance, generally require cryogenic temperatures. Because of its simplicity and proven utility, photoreflectance has recently gained importance for the evaluation of semiconductor thin films and heterostructures.

As pointed out in the aforementioned applications, the basic idea of modulation spectroscopy is a very general principle of experimental physics. Instead of directly measuring an optical spectrum, the derivative with respect to some parameter is evaluated. This can easily be accomplished by external or internal modulation of some parameter of the sample or measuring system in a periodic fashion and measuring the corresponding normalized change in the optical properties. In photoreflectance, the built-in electric field of the materials is modulated by the photo-injection of electron-hole pairs created by a pump beam of wavelength $\lambda_p$ which is chopped at frequency $\Omega_m$.

An improved apparatus utilizing photoreflectance, which will be described by reference to FIG. 1, is disclosed in the aforementioned application Ser. No. 07/408,903, which enables achievement of improved signal-to-noise ratios, to further eliminate problems encountered in the prior art apparatus and in particular to utilize novel computerized procedures to gain additional information on the characteristics of the materials examined.

Accordingly, it is an object of the present invention to provide an improved method for in-situ determination of the Fermi level in GaAs and similar materials by photoreflectance which avoids by simple means the shortcomings and drawbacks encountered in the prior art.

Another object of the present invention resides in a method which permits in-situ determination of the Fermi level in GaAs and similar materials with great accuracy by simple means.

A further object of the present invention resides in a method utilizing photoreflectance for determining the Fermi level of certain materials in situ, for example, in the MBE growth chamber of the material, which is simple to use, provides relatively great accuracy in the information which can be obtained and assures high reliability.

Still another object of the present invention resides in a method utilizing computer technologies to obtain in-situ information on the Fermi level of GaAs and similar materials.

BRIEF DESCRIPTION OF THE DRAWINGS

These and other objects, features and advantages of the present invention will become more apparent from the following description when taken in connection with the accompanying drawing which shows, for purposes of illustration only, one embodiment in accordance with the present invention, and wherein.

DETAILED DESCRIPTION OF THE DRAWINGS

Figure 1:
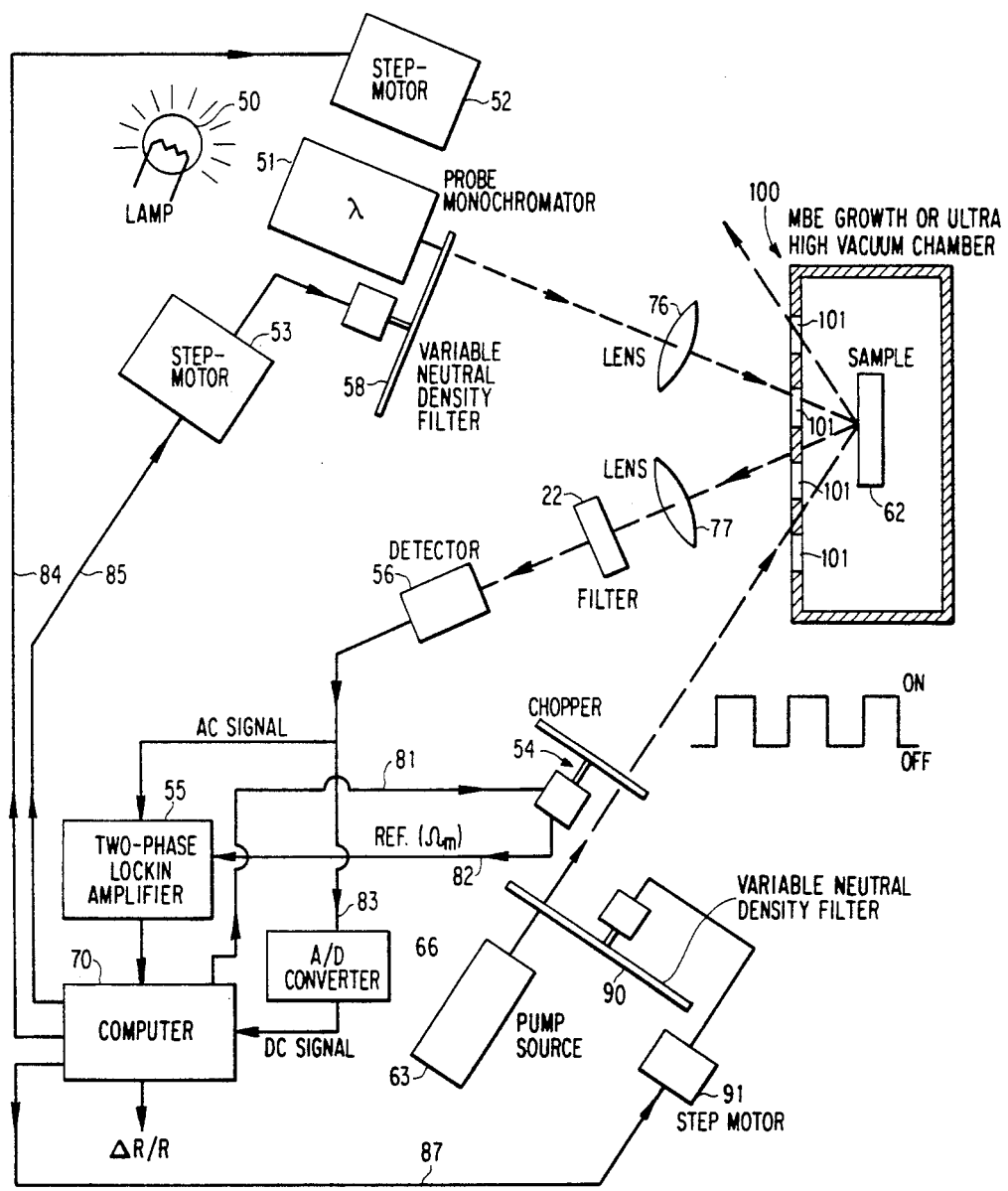
FIG. 1 is a schematic block diagram of an apparatus in accordance with the present invention which utilizes photoreflectance in combination with computer controls to increase accuracy and versatility of the equipment.

Referring now to the drawing, and more particularly to FIG. 1, reference numeral 50 designates an appropriate lamp source whose light passes through a monochromator 51, to be referred to hereinafter also as probe monochromator. The exit intensity of the monochromator 51 at the wavelength λ is focused onto a sample 62 by means of conventional lenses or mirrors. For in-situ measurements, the sample 62 is located within a schematically illustrated MBE growth chamber generally designated by reference numeral 100 and of any conventional construction which is provided with a number of vacuum-sealed ports 101 for the passage of light, as required. $I_o(\lambda)$ is thereby the intensity of light from the probe source 50, 51 striking the sample 62. Electromodulation of the sample 62 is produced by photoexcitation of electron-hole pairs created by a pump beam from a pump source 63. The pump beam can be a laser or a monochromator and is chopped by a conventional chopper 54 at a frequency $\Omega_m$. The beam reflected from the sample 62 is again collected by conventional second lenses 77 or mirrors and is focused on a detector 56, such as a photomultiplier, photodiode, photoconductor, etc. Although FIG. 1 shows the configuration for reflectance, the experiment can also be readily modified for transmission by placing the detector behind the sample. Accordingly, the term photoreflectance (PR) is used in this application in a broad sense to encompass both reflectance and transmittance.

The output of the detector 56 contains two signals, i.e., the d.c. signal and the a.c. signal. The d.c. signal is applied to a computer generally designated by reference numeral 70 by way of A/D converter 66. The a.c. signal from the detector 56 is applied to a lock-in amplifier 55 which also receives a reference signal $\Omega_m$ from the chopper 54. The desired signal $\Delta R/R$ contained in the output of the lock-in amplifier 55 is applied to computer 70.

The probe monochromator 51 is driven by step-motor 52 which is controlled by the computer 70 of any conventional construction, programmed by conventional techniques to achieve the various functions, as described more fully in the aforementioned application Ser. No. 07/408,903, the subject matter of which is incorporated herein by reference. The variable neutral density filter 58 is driven by a step-motor 53 which is also controlled by the computer 70. It has been found that the signal-to-noise ratio can be improved by a factor of 10 using a step-motor control. In addition, the computer 70 also controls the frequency ($\Omega_m$) of the modulator 54, for instance, in the form of a conventional chopper modulating the pump beam emitted by the pump source 63. Furthermore, the lock-in amplifier 55 is a two-phase model of known construction which determines the in-phase and out-phase components of the photoreflectance signal (relative to the pump beam). The use of the two-phase lock-in amplifier 55 permits evaluation of the photoreflectance signal as a function of $\Omega_m$ to yield information about trap states. It has also been found that signals from different depth regions of a sample structure produce signals with different phases and dependence on $\Omega_m$ which can be sorted out by the two-phase lock-in amplifier 55 and the computer-controlled modulating frequency $\Omega_m$.

OPERATION

After normalization of the apparatus as described in the aforementioned applications, the apparatus is ready for use to undertake certain tests including the tests for the in-situ determination of the Fermi level in GaAs and similar materials. A typical operation is as follows:

In the apparatus according to FIG. 1, the probe light produced by lamp 50 in conjunction with the probe monochromator 51, which can be adjusted by step-motor 52 to vary the wavelength of the probe light, is directed onto sample 62 by the use of a lens(es) or mirror(s), schematically indicated by lens 76. The pump beam produced by the pump source 63 in the form of a laser or other appropriate secondary light source is also directed onto the sample 62 after being modulated by modulator 54 whose frequency $\Omega_m$ can be varied by computer 70 by way of line 81. The light reflected (transmitted) from the sample 62 is then directed onto detector 54 by a lens(es) or mirror(s), schematically indicated by lens 77. A filter 22 ma be interposed in the optical path between the sample 62 and detector 54. The a.c signal in the output of detector 54 is then applied to the input of the two-phase lock-in amplifier 55 to which is also applied a reference signal ($\Omega_m$) from the modulator 54 by way of line 82 to provide information about the modulating frequency $\Omega_m$. The d.c. signal from detector 54 is applied to computer 70 by way of line 83 which includes an A/D converter 66 to change the analog signal from detector 54 into a digital signal for use by the computer 70.

One output of computer 70 contains the desired photoreflectance signal $\Delta R/R$ which can be applied to user-friendly displays, e.g a display screen (not shown) associated with the computer. Another output of computer 70 controls the step-motor 52 to vary the probe-light wavelength λ, by way of line 84. A further output of computer 70 controls the step-motor 53 to vary the adjustment of the variable neutral-density filter 58 by way of line 85, and still another output of computer 70 controls the frequency $\Omega_m$ of the modulator 54 by way of line 81.

In-Situ Determination of Fermi Level in GaAs and Similar Materials

Utilizing the apparatus and its operation described by reference to FIG. 1, it has now been found that the Fermi level ($V_F$) can be determined in situ with relatively great accuracy on GaAs and similar materials even though $V_F$ is the intrinsic property of the material in a given environment. Any absolute determination of $V_F$ therefore changes depending on environmental conditions and level thereof. Furthermore, in practice the determination of $V_F$ is complicated because light also produces certain surface voltage ($V_S$) effects.

At the surface and interface of GaAs, it is well known that the Fermi level ($V_F$) is pinned in the energy gap by surface states. Thus, $V_F$ at most metal/GaAs interfaces is nearly invariant for a wide range of metal work functions. However, the position of $V_F$ at the surface cannot simply be derived from its bulk value but has to be measured separately for every surface, each of which may differ by crystallographic orientation or environment. Most studies of $V_F$ have involved heretofore soft X-ray photoemission (PES). However, surface photovoltage ($V_S$) effects in PES are significant. Thus $V_S$ must also be considered in other optical probes of $V_F$ such as photoreflectance, where the measured barrier height $V_M$ is also the difference between $V_F$ and $V_S$ ($V_M = V_F - V_S$).

In order to explore the role of environment and $V_S$ on the evaluation of $V_F$, photoreflectance has been used according to the present invention to study the surface barrier height on (100) MBE-grown n- and p-GaAs both in-situ in the MBE growth chamber and after exposure to air. To determine the role of photocurrents on $V_F$, measurements were performed by the use of apparatus described by reference to FIG. 1 as a function of temperature (77 K.<T<450 K.) and light intensity of both the probe ($I_{pr}$) and pump ($I_{pu}$) beams which were varied by means of neutral density filter 58 and neutral density filter 90 in the path of the pump beam and controlled from computer 70 by way of line 87 with the use of a stepping motor 91. The n-and-p samples had a well controlled electric field (F) created by fabricating an undoped layer of thickness L on a buried 1 μm (a) Si-doped ($n \sim 2 \times 10^{18} cm^{-3}$) buffer on an n+ substrate or (b) Be-doped ($p \sim 4 \times 10^{18} cm^{-3}$) buffer on a p+ substrate, respectively. The pump beam was the 633 nm line of a He-Ne laser chopped at 100 Hz.

Figure 2:
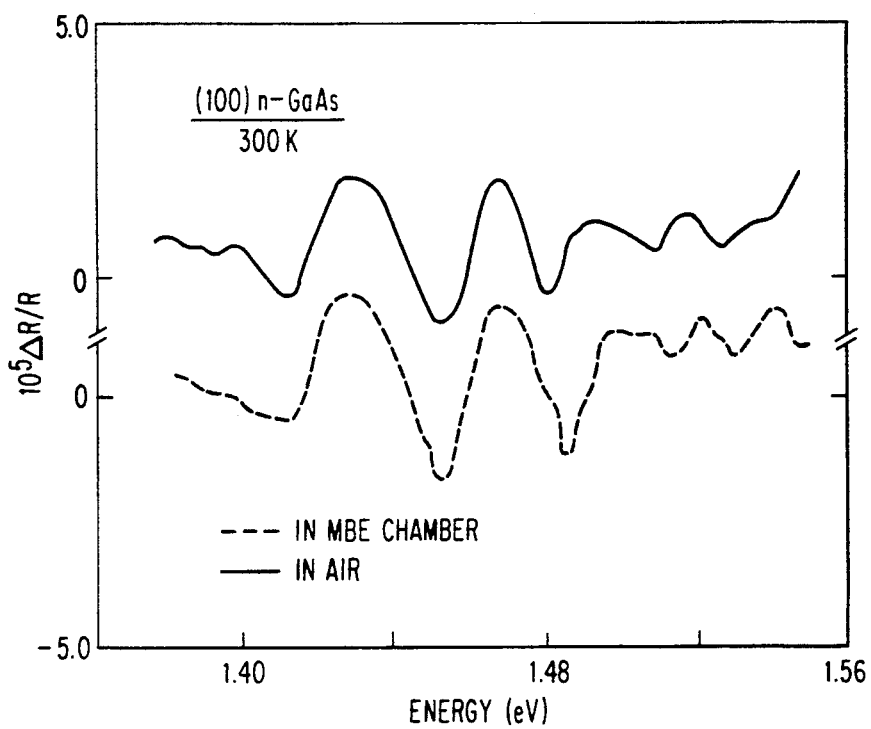
FIG. 2 is a graph of the photoreflectance spectra in the MBE chamber and after exposure to air with a (100) n-GaAs sample at 300 K. temperature.
Figure 3:
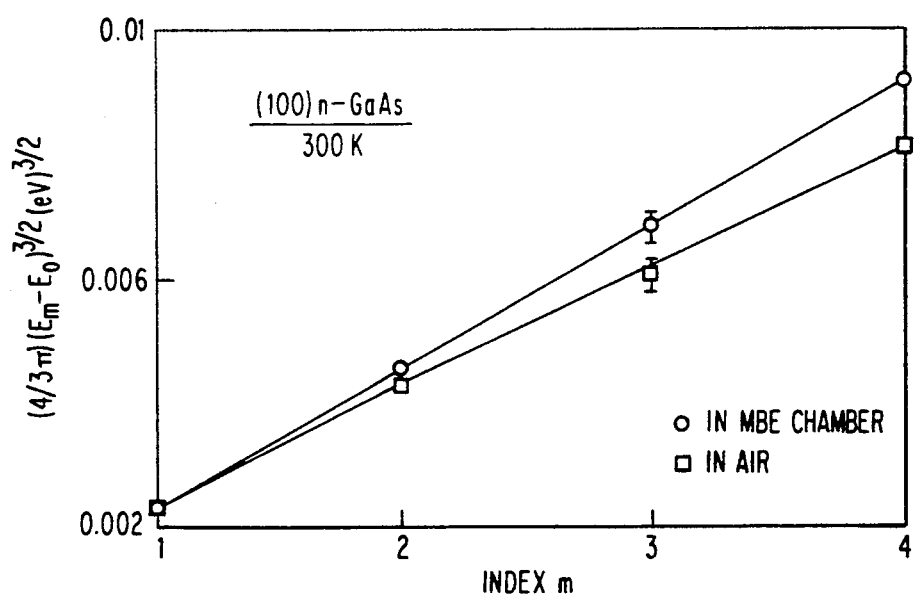
FIG. 3 is a graph of $(4/3\pi)(E_m-E_o)^{3/2}$ as a function of the index m for the (100) n-GaAs sample at 300 K. temperature.

Shown by the solid and dashed lines in FIG. 2 are the photoreflectance spectra of the n-sample (L=228 nm) at 300 K. in the ultra-high vacuum (UHV) MBVE chamber and immediately after exposure to air, respectively, with $I_{pu} = 10$ μW/cm² and $I_{pr} = 2$ μW/cm². Similar results were obtained for the p-sample. The field F can be determined from the observed Franz-Keldysh oscillations (FKO) from the slot of $(4/3\pi) (E_m - E_o)^{3/2}$ as a function of m (the index of the mth FKO extrema), where $E_m$ is the energy of the mth extrema and $E_o$ is the band-gap. This plot is shown in FIG. 3. The measured barrier height $V_m(=V_F - V_S)$ is given by $V_m = FL + [\epsilon F^2/2qn(p)] + (kT/q)$, where $\epsilon$ is the static dielectric constant of GaAs and n(p) are the carrier concentrations in the buffer layers.

From the above analysis for the n- and P-samples in UHV and in air the following values of $V_m$ relative to the conduction and valence bonds, respectively, were found: $V_m{}^n(UHV) = 0.69 \pm 09.025$ V, $V_m{}^n(air) = 0.57 \pm 0.025$ V, $V_m{}^p(UHV) = 0.74 \pm 0.035$ V and $V_m{}^p(air) = 0.66 \pm 0.035$ V. There is a significant difference in surface potential between the UHV and air exposed surfaces. First, it can be seen that $[V_m{}^n(UHV) + V_m{}^p(UHV)] = 1.43$ eV, (the band gap energy for GaAs) and is greater than the sum of the n and p surface potentials for air-exposed surfaces (=1.23 eV). Therefore, the air-exposed surface is more "flat band" and hence less "pinned" than the UHV surfaces. This difference can be understood from the following considerations. FIG. 3 shows that surface state density and hence "pinning intensity" is correlated with the degree of misorientation for (100) surfaces. This in turn correlates with atomic step density. Furthermore, FIG. 3 shows that there is increased chemical reactivity at these atomic steps. If so, enhanced selective oxidation at atomic steps during air exposure might be expected. Therefore, to explain the results of this work, it is surmised that in the UHV condition there is a maximum in surface state density due to "unpassivated" atomic steps. Air exposure causes preferential oxidation and hence passivation at the atomic steps. This in turn reduces the surface state density and hence the pinning density.

Figure 4:
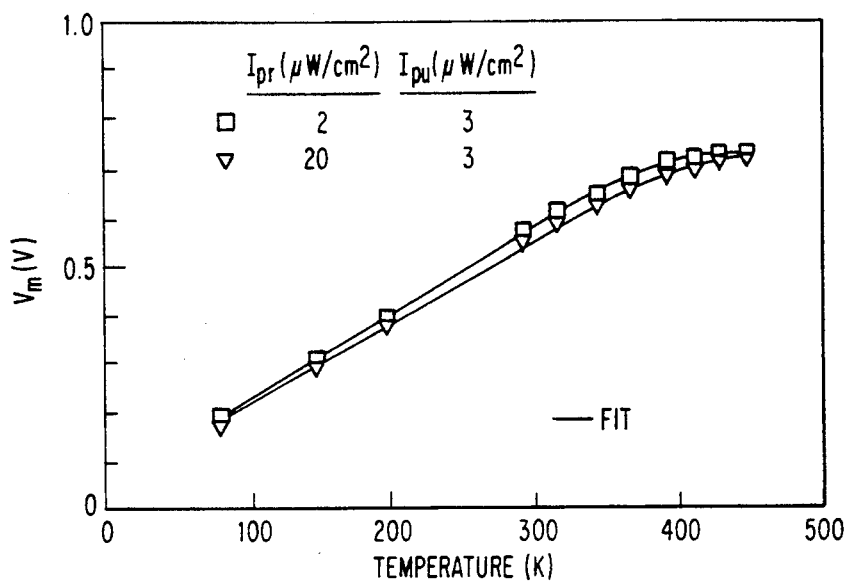
FIG. 4 is a graph of the measured barrier height (Vm) as a function of temperature and light intensity.

On an n-sample (L=110 nm) that had been exposed to air for several days, the effects of temperature and light intensity were also determined. Shown in FIG. 4 are $V_m$ for 77<K.<450 K. for $I_{pu} = 3$ μW/cm² and $I_{pr} = 2$ and 20 μw/cm². Up to about 350 K. the variation of $V_m$ with T is approximately linear and then saturates at higher temperatures; for larger $I_{pr}$ this saturates shifts to higher T. The solid lines are least-squares fits.

$$V_m = V_F - (\eta kT/q) \ln \{[J_{pc}/J_o(T)] \exp (qV_F/kT) + 1\} \quad (1)$$

where $\eta$ is an ideality factor, $J_{pc}$ is the induced photocurrent and $J_o(T)$ is saturation current which depends on the dominant current flow mechanism.

For the sample configuration and temperature range, diffusion and thermionic emission are the main contribution to $J_o(T)$. One can write that $J_o(T) = AT^2/(1 + BT^{\frac{1}{2}})$, with $A = 8.0$ A/cm²−K² and $B = 3.3 \times 10^{-4} K^{3/2}$. Because of this temperature dependence of $J_o(T)$ and the factor exp ($qV_F/kT$) in Equation (1), at sufficiently high temperatures $V_S$ becomes negligible and hence $V_m$ approaches $V_F$. The results for $V_F = 0.73 \pm 0.02$ V obtained in accordance with the present invention are in good agreement with other measurements.

Tests were also conducted by the use of photoreflectance to determine surface photovoltage ($V_S$) effects on the determination of Fermi level pinning ($V_F$) on (100) n-GaAs in air and with W-metal coverage (in-situ) as a function of temperature (77 K.<T<450 K.) and light intensity (I). The effect of metal coverage is to reduce the influence of $V_S$.

More particularly, these photoreflectance tests were conducted to determine the effects of $V_S$ on (100) n-GaAs as a function of temperature (77 K.<T<450 K.), light intensity of the pump beam ($I_{pu}$), of the probe beam ($I_{pr}$) and of the dc ($I_{dc}$) beams and W-metal coverage. The latter were performed in-situ in an ultrahigh vacuum (UHV) chamber. Photoreflectance measurements were made on a GaAs structure that again contained a well-controlled electric field (F) in the depletion region. From the observed Franz-Keldysh oscillations (FKO), it was possible to accurately determine F and hence $V_S$. These tests confirmed the dependence of $V_S$ on temperature and light intensity. It was found that $V_S$ varies considerably with temperature and becomes negligible (at low light levels) at about 400 K. yielding a value of $V_F = 0.73 \pm 0.02$ volts. The effect of metal coverage is to reduce the influence of $V_S$ so that $V_m = V_F$ at lower temperatures. These tests involved in the present invention demonstrate the considerable utility of photoreflectance for the study of environment on the electronic properties of semiconductor surfaces, including metallization. In addition, they have also served to elucidate the mechanism of photoreflectance in relation to the photovoltage effect.

The structure used in this study was prepared by molecular beam epitaxy (MBE) by fabricating an undoped layer of thickness L (=110 nm) on a buried 1 μm Si-doped buffer ($n \sim 2 \times 10^{18} cm^{-3}$) on an n+ substrate. The field F is almost constant in the undoped region between the buried layer and surface. The thickness L was evaluated from a C-V measurement. The pump beam was the 633 nm line of a He-Ne laser chopped at 100 Hz. A second He-NE laser was used to produce $I_{dc}$. The values of $I_{pu}$, $I_{pr}$ and $I_{dc}$ were controlled by neutral density filters. The study of W-metal coverage was performed in-situ in an UHV chamber with an operating pressure of better than $1.5 \times 10^{-10}$ torr.

Figure 5:
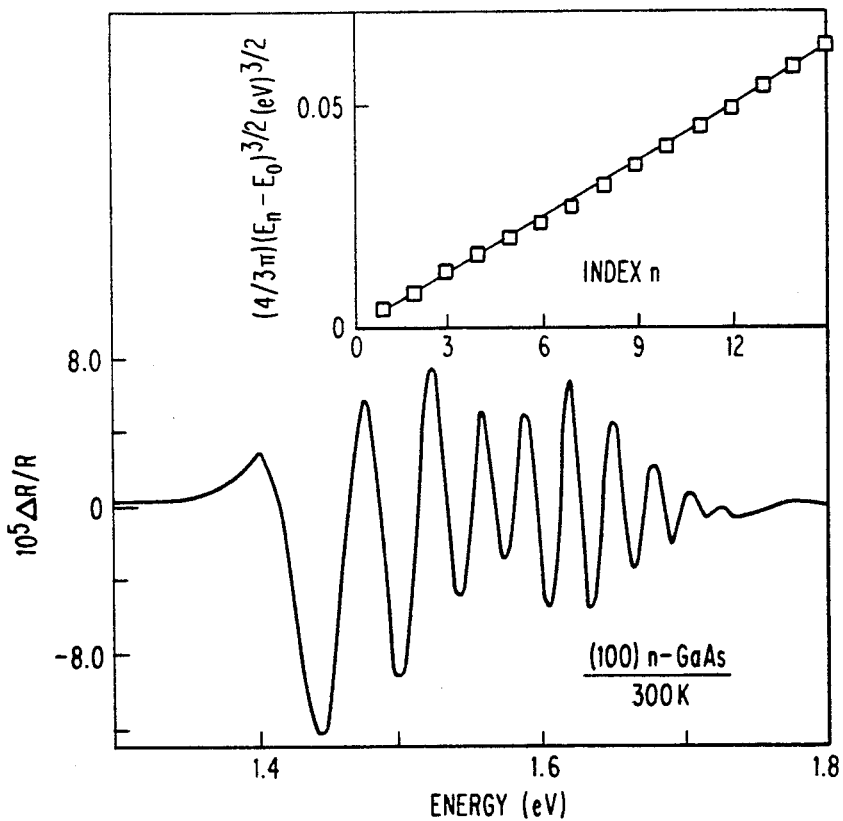
FIG. 5 is a photoreflectance spectrum at room temperature with $I_pu=3$ $\mu W/cm^2$ and $I_pr=2$ $\mu W/cm^2$ for a (100) n-GaAs sample at 300 K. temperature, the inset showing a graph of $(4/3\pi)(E_n-E_o)^{3/2}$ as a function of index n.

Shown in FIG. 5 is the photoreflectance spectrum of the sample in air at 300 K. with $I_{pu} = 3$ μW/cm² and $I_{pr} = 2$ μW/cm². FIG. 5 exhibits a large number of Franz Keldysh oscillations (FKO) because of the high field and small broadening parameter in the undoped region. The extrema in the FKO are given by:

$$n\pi = \phi + (4/3) [(E_n - E_o)/\zeta\theta]^{3/2} \quad (2)$$

and can be used to determine F. The quantity n is the index of the $n^{th}$ extrema, $\phi$ is an arbitrary phase factor, $E_n$ is the photon energy of the $n^{th}$ extrema and $E_o$ is the energy gap. The electrooptic energy $\zeta\theta$ is:

$$(\zeta\theta)^3 = e^2\zeta^2 F^2/2\mu \tag{3}$$

$\mu$ being the reduced interband effective mass for the electron and heavy-hole pair in the direction of F. Plotted in the inset of FIG. 5 is the quantity $(4/3)(E_n - E_o)^{3/2}$ as a function of index n. The solid line is a least-squares fit to Equation (2) yielding a value of $F = 5.06 \times 10^4$ V/cm with $= 0.055$ (in units of free electron mass).

The measured barrier height $V_m (= V_F - V_S)$ can again be determined from $$V_m = FL + (\epsilon F^2/2qn) + (kT/q) \tag{4}$$

where $\epsilon$ is the static dielectric constant of GaAs and n is the doping level in the buffer.

Figure 6:
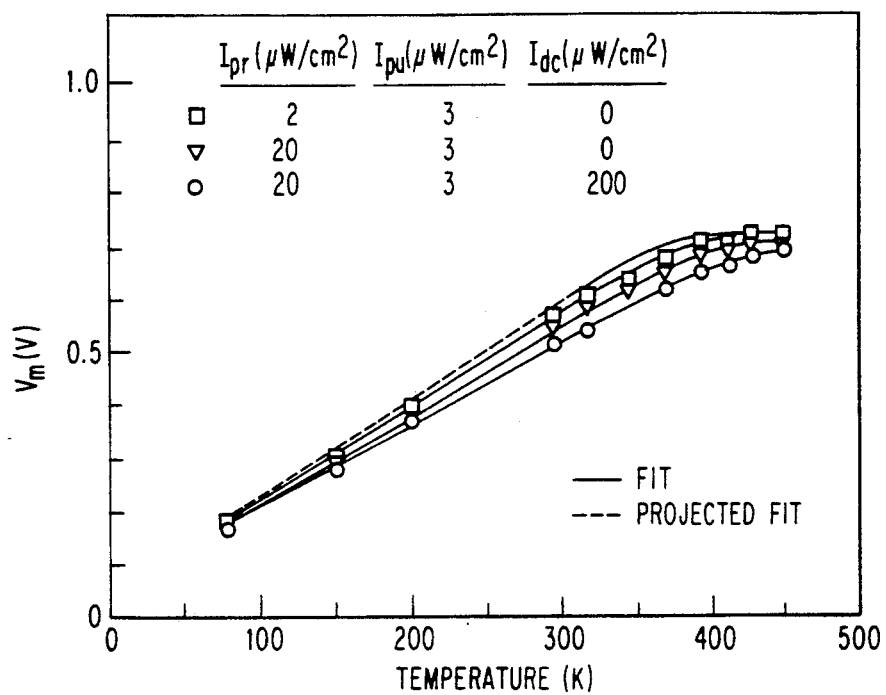
FIG. 6 is a graph of the measured barrier height $V_m$ as a function of temperature and light intensity, the solid lines being least-squares fits to Equation (5) with the dash lines representing a generated curve corresponding to a light intensity of 0.4 $\mu W/cm^2$.

FIG. 6 illustrates the values of $V_m$ as a function of temperature for various values of $I_{pu}$, $I_{pr}$ and $I_{dc}$. No hysteresis of $V_m$ was found with temperature cycling. For the lowest light intensity $V_m$ saturates at about 400 K. Higher intensities decrease $V_m$ (i.e., greater $V_S$) at a given temperature and shift the saturation to higher temperatures. The solid lines in FIG. 6 are least-squares fits to:

$$V_m = V_F - (\eta kT/q) \ln \{[J_{pc}/J_o(T)] \exp(qV_F/kT) + 1\} \tag{5}$$

where $\eta$ is an ideality factor, $J_{pc}$ is the induced photocurrent and $J_o(T)$ is the saturation current which depends on the dominant current flow mechanism.

For the sample configuration and temperature range used in these tests, diffusion and thermionic-emission are the main contributions to $J_o(T)$ so that one can write:

$$J_o(T) = AT^2/(1 + BT^{3/2}) \tag{6}$$

with $A = 8.0$ $A/cm^2 - K^2$ and $B = 3.3 \times 10^{-4}$ $K^{-3/2}$. Since $J_o(T)$ increases rapidly with temperature and because of the factor $\exp(qV_F/kT)$ in Equation (5), at sufficiently high temperatures $V_S$ becomes negligible and hence $V_m$ approaches $V_F$. An analysis according to the present invention yields $\eta = 0.91$, $V_F = 0.73 \pm 0.02$ V and $J_{pc} = (1.1 + 0.6) \times 10^{-4}$ $A/cm^2$ (for the lowest light level). At higher intensities correspondingly larger values of $J_{pc}$ were found. The foregoing determination of $V_F$ is in good agreement with other measurements. Furthermore, to illustrate the importance of $V_S$, even at low light levels, the dashed line is plotted in FIG. 6 which corresponds to a light intensity of 0.4 $\mu$W/cm$^2$.

Figure 7:
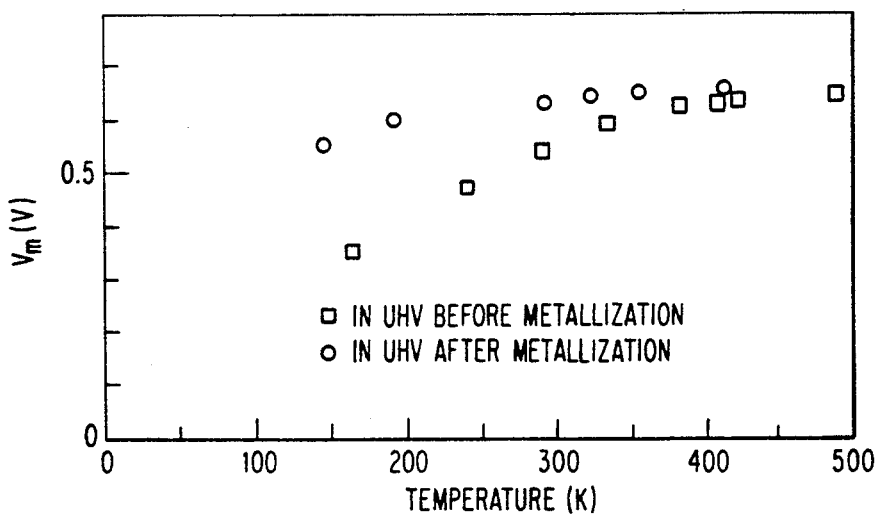
FIG. 7 is a plot of the values of $V_m$ in an ultrahigh vacuum chamber before and after W-metallization as a function of temperature.

After completing the measurements in air, the sample was placed in a UHV chamber. FIG. 7 shows $V_m$ as a function of temperature before and after a deposition of four monolayers of W with $I_{pu} = 40$ $\mu$W/cm$^2$ and $I_{pr} = 10$ $\mu$w/cm$^2$. No attempt was made to clean the sample before metallization. Note that $V_F = 0.65 \pm 0.02$ V in the UHV chamber before deposition. The effect of the metal is to shift the saturation to much lower temperatures although $V_F$ remains the same before and after metallization. The application of the metal creates an equipotential surfaces, in contrast to the bare surface which is insulating. The ability of the diode to discharge the surface is enhanced and hence $V_S$ is reduced. There is also a small effect of the absorption of the metal which reduces $J_{pco}$ and hence $V_S$.

The present invention thus establishes the effects of $V_S$ on $V_m (= V_F - V_S)$ from a material such as (100) n-GaAs structure with well-controlled F as a function of T and I in the range 77 K. $< T <$ 450 K. It confirms that $V_S$ is dependent on light intensity and temperature, whereby $V_S$ with a decrease in light intensity and approaches 0 as the light intensity approaches 0. By contrast, an increase in temperature causes a decrease in $V_S$ as shown in FIG. 7. The W-metal coverage (in-situ) was found to reduce the effect of $V_S$. Additionally, the present invention also confirms the usefulness of photoreflectance combined with such semiconductor structures, for the investigation of environment on the determination of $V_F$, including in-situ studies.

While we have shown and described several embodiments in accordance with the present invention, it is understood that the same is not limited thereto but is susceptible of numerous changes and modifications as known to those skilled in the art, and we therefore do not wish to be limited to the details shown and described herein but intend to cover all such changes and modifications as are encompassed by the scope of the appended claims.

We claim:

1. A method for determining in-situ the Fermi level ($V_F$) at the surfaces or interfaces of GaAs and related materials by photoreflectance, comprising the steps of
   (a) directing a probe beam of monochromatic light onto a sample of such material,
   (b) electromodulating the sample by directing onto the same a modulated pump beam from a pump source to thereby modulate the built-in electric field at the surface/interface of the material,
   (c) collecting the light reflected from or transmitted by a sample in a detector which produces a signal containing information on the measured barrier height $V_m = V_F - V_S$, where $V_S$ represents the surface voltage effect on the sample by the photoreflectance, and
   (d) repeating the tests while varying a parameter affecting the numerical value of $V_S$ until changes in the parameter will provide only small changes in $V_S$, thereby indicating that $V_S$ approaches zero and therewith the obtained information represents substantially the Fermi level $V_F$.

2. A method according to claim 1, wherein the in situ tests are performed in an molecular beam epitaxy growth chamber under vacuum.

3. A method according to claim 2, wherein the in situ tests under vacuum in the molecular beam epitaxy growth chamber are followed by similar tests after exposure of the sample to air.

4. A method according to claim 2, wherein the parameter is temperature.

5. A method according to claim 2, wherein the parameter is light intensity.

6. A method according to claim 1, wherein the material sample includes a metal coverage.

7. A method according to claim 6, wherein the coverage is a W-metal.

8. A method according to claim 6, wherein the in situ tests are performed in an ultra-high vacuum or in an molecular beam epitaxy growth chamber under vacuum.

9. A method according to claim 8, wherein the in situ tests under vacuum in the molecular beam epitaxy growth chamber are followed by similar tests after exposure of the sample to air.

10. A method according to claim 1, characterized in that Franz-Keldysh oscillations are used to determine the measured barrier height $V_m$.

* * * * *